(12) United States Patent
Gollier et al.

(10) Patent No.: US 7,599,055 B2
(45) Date of Patent: Oct. 6, 2009

(54) SWEPT WAVELENGTH IMAGING OPTICAL INTERROGATION SYSTEM AND METHOD FOR USING SAME

(75) Inventors: Jacques Gollier, Painted Post, NY (US); Qi Wu, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 323 days.

(21) Appl. No.: 11/711,207

(22) Filed: Feb. 27, 2007

(65) Prior Publication Data

US 2008/0204760 A1    Aug. 28, 2008

(51) Int. Cl.
*G01N 1/10*    (2006.01)
(52) U.S. Cl. ........................ 356/246; 356/326
(58) Field of Classification Search ................. 356/244, 356/246, 445–448, 432–440, 326
See application file for complete search history.

(56) References Cited

U.S. PATENT DOCUMENTS

| | | | |
|---|---|---|---|
| 4,815,843 A | | 3/1989 | Tiefenthaler et al. ........ 356/128 |
| 6,429,022 B1* | | 8/2002 | Kunz et al. ................. 436/164 |
| 7,142,296 B2* | | 11/2006 | Cunningham et al. ....... 356/326 |
| 2003/0059855 A1* | | 3/2003 | Cunningham et al. ........ 435/7.9 |
| 2004/0223881 A1* | | 11/2004 | Cunningham et al. .... 422/82.05 |
| 2004/0248318 A1* | | 12/2004 | Weinberger et al. ......... 436/173 |
| 2005/0227374 A1 | | 10/2005 | Cunningham ............... 436/518 |
| 2006/0141527 A1 | | 6/2006 | Caracci et al. ................ 435/7.1 |
| 2007/0252987 A1* | | 11/2007 | Cunningham et al. ....... 356/326 |
| 2009/0032690 A1* | | 2/2009 | Modavis ................ 250/227.27 |

FOREIGN PATENT DOCUMENTS

| | | |
|---|---|---|
| EP | 1 031 828 | 8/2000 |
| WO | 2004/092730 | 10/2004 |

OTHER PUBLICATIONS

Ph.M. Nellen et al., "Integrated Optical Input Grating Couplers as Biochemical Sensors", Sensors and Actuators, vol. 15, 1988, pp. 285-295.
J.P. Golden et al., "A Comparison of Imaging Methods For Use in An Array Biosensor", Biosensors and Bioelectronics, vol. 17, 2002, pp. 719-725.
P.Y. Li et al., "A New Method For Label-Free Imaging Of Biomolecular Interactions", Sensors and Actuators B, vol. 99, 2004, pp. 6-13.
C.E. Jordan et al., "Surface Plasmon Resonance Imaging Measurements of DNA Hybridization Adsorption and Streptavidin/DNA, Multilayer Formation at Chemically Modified Gold Surfaces", Anal. Chem, 1997, vol. 69, pp. 4939-4947.

(Continued)

*Primary Examiner*—Hoa Q Pham
(74) *Attorney, Agent, or Firm*—Timothy M. Schaeberle; Thomas R. Beall; William J. Tucker

(57) ABSTRACT

A swept wavelength imaging optical interrogation system and a method for using the same to interrogate one or more biosensors are described herein. The swept wavelength imaging optical interrogation system is built upon a swept wavelength optical interrogation technology where a 2-D label free image is extracted from a series of high speed spectral images of the biosensor(s) without the need of performing mechanical scanning.

23 Claims, 11 Drawing Sheets

OTHER PUBLICATIONS

Z.H. Wang et al., "A Label-Free Multisensing Immunosensor Based on Imaging Ellipsometry", Anal. Chem., 2003, vol. 75, pp. 6119-6123.

J.P. Landry et al., "Label-Free Detection of Microarrays of Biomolecules by Oblique-Incidence Reflectivity Difference Microscopy", Optics Letters, Mar. 15, 2004, vol. 29, No. 6, pp. 581-583.

M. Piliarik et al., "A New Surface Plasmon Resonance Sensor For High-Throughput Screening Applications", Biosensor and Bioelectronics: vol. 20, 2005, pp. 2104-2110.

G.J. Wegner et al., "Characterization and Optimization of Peptide Arrays for the Study of Epitope—Antibody Interactions Using Surface Plasmon Resonance Imaging", Anal. Chem., 2002, vol. 74, pp. 5161-5168.

G.J. Wegner et al., "Real-Time Surface Plasmon Resonance Imaging Measurements for the Multiplexed Determination of Protein Adsorption/Desorption Kinetics and Surface Enzymatic Reactions on Peptide Microarrays", Anal. Chem., 2004, vol. 76, pp. 5677-5684.

J.M. Jung et al., "A Fusion Protein Expression Analysis Using Surface Plasmon Resonance Imaging", Analytical Biochemistry, vol. 330 2004, pp. 251-256.

V. Kanda et al., "Label-Free Reading of Microarray-Based Immunoassays With Surface Plasmon Resonance Imaging", Anal. Chem., 2004 vol. 76, pp. 7257-7262.

C.R. Mace et al., "Theoretical and Experimental Analysis of Arrayed Imaging Reflectometry as a Sensitive Proteomics Technique", Anal. Chem., 2006, vol. 78, pp. 5578-5583.

\* cited by examiner

SWEPT WAVELENGTH IMAGING OPTICAL INTERROGATION SYSTEM AND METHOD FOR USING SAME

TECHNICAL FIELD

The present invention relates to a swept wavelength imaging optical interrogation system and a method for using the same to interrogate one or more biosensors. In one embodiment, the biosensors are incorporated within the wells of a microplate.

BACKGROUND

Today non-contact optical sensor technology is used in many areas of biological research to help perform increasingly sensitive and time-constrained assays. In one application, an optical interrogation system can be used to monitor changes in the refractive index or variations in the optical response/optical resonance of an optical biosensor as a biological substance is brought into a sensing region of the biosensor. The presence of the biological substance alters the optical resonance of the biosensor when it causes a biochemical interaction like material binding, adsorption etc. . . . It is this alteration of the optical resonance that enables one to use the biosensor to directly monitor a biological event in label-free assays. Examples of biosensors include surface plasmon resonance (SPR) sensors and waveguide grating coupler (WGC) sensors. A detailed discussion about the structure and function of the WGC sensor is provided in the following documents:

- U.S. Pat. No. 4,815,843 entitled "Optical Sensor for Selective Detection of Substances and/or for the Detection of Refractive Index Changes in Gaseous, Liquid, Solid and Porous Samples".
- K. Tiefenthaler et al. "Integrated Optical Switches and Gas Sensors" Opt. Lett. 10, No. 4, April 1984, pp. 137-139.
- Ph. M. Nellen, K Tiefenthaler, W. Lukosz, "Integrated Optical Input Grating Couplers as Biochemical Sensors" Sensors and Actuators, 15, 273 (1988)

The contents of these documents are incorporated by reference herein.

The optical interrogation system used today to interrogate the biosensor can take many forms, and two of the more general forms are briefly described next. In one case, the optical interrogation system delivers a single-wavelength, high-angular content optical beam to the biosensor, and the output beam received from the biosensor provides some information about the angular response of the biosensor. This type of optical interrogation system is commonly referred to as an angular interrogation system since angular detection is employed to locate a dominant angle in the output beam which is indicative of the particular optical response/optical resonance of the biosensor. In another case, the optical interrogation system delivers a collimated optical beam containing a range of wavelengths to the biosensor, the output beam received from the biosensor provides some information about the wavelength response of the biosensor. This type of optical interrogation system is commonly referred to as a spectral interrogation system since the spectrum of the output beam is analyzed to locate the resonant wavelength in the output beam which is indicative of the particular optical response/optical resonance of the biosensor.

These types of optical interrogation systems work well but there is still a desire to try and design a new and improved optical interrogation system that can be used to interrogate a biosensor to determine if a biomolecular binding event (e.g., binding of a drug to a protein) or other event occurred on a surface of the biosensor. One such optical interrogation system which uses a swept wavelength tunable laser to interrogate one or more biosensors is the subject of the present invention.

SUMMARY

The present invention includes a swept wavelength imaging optical interrogation system and a method for using the same to interrogate one or more biosensors. In one embodiment, the swept wavelength imaging optical interrogation system includes: (a) a tunable laser that has a tuning range wherein an optical beam is emitted therefrom which has a predetermined sequence of distinct wavelengths over a predetermined time period; (b) illumination optics that converts the optical beam into one or more interrogation beams which illuminate one or more biosensors; (c) imaging optics that collects an image from the illuminated one or more biosensors; (d) a 2-D imaging device that obtains a sequence of the collected images each of which corresponds with one of the distinct wavelengths of the optical beam emitted from the tunable laser; and (e) a data processing device that receives the collected images and processes the collected images to determine for example if a biological event occurred on one or more of the biosensors.

BRIEF DESCRIPTION OF THE DRAWINGS

A more complete understanding of the present invention may be had by reference to the following detailed description when taken in conjunction with the accompanying drawings wherein.

DETAILED DESCRIPTION

Figure 1:
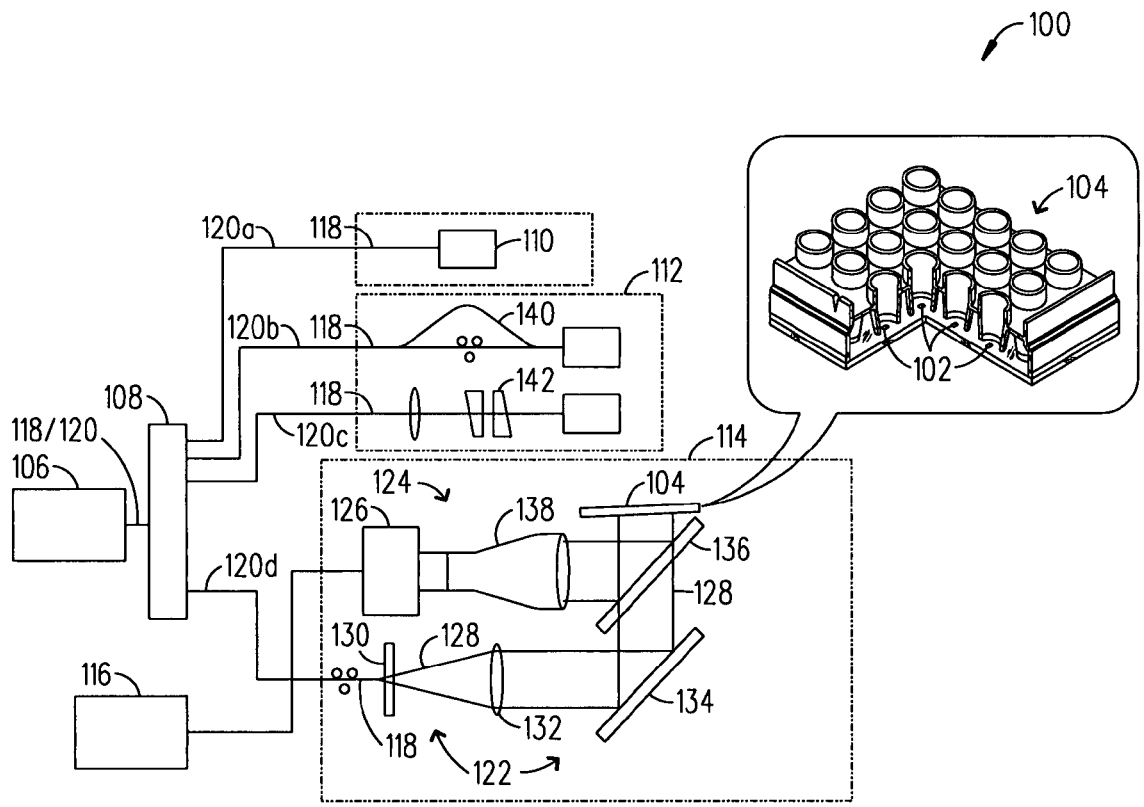
FIG. 1 is a block diagram of an exemplary swept wavelength imaging optical interrogation system which is used to interrogate one or more biosensors in accordance with the present invention.

Referring to FIG. 1, there is a block diagram of an exemplary swept wavelength imaging optical interrogation system 100 that can be used to interrogate one or more biosensors 102 in accordance with the present invention (note: the biosensors 102 are shown located within the wells of a microplate 104). The optical interrogation system 100 includes a tunable laser 106, a 1×4 splitter 108, a power tracking device 110, a wavelength tracking device 112, an imaging system 114 and a data processing device 116. The tunable laser 106 (e.g., swept wavelength tunable laser 106) emits an optical beam 118 which has a predetermined sequence of distinct wavelengths over a predetermined time period. For instance, the tunable laser 106 can have a tuning range where the optical beam 118 emitted sequences through 838 nm to 853 nm without mode hop at a tuning speed of 0.1 nm/sec to 300 nm/sec. The tunable laser 106 is shown emitting the optical beam 118 into a fiber optic cable 120 which is connected to the 1×4 splitter 108.

In this example, the 1×4 splitter 108 receives the optical beam 118 and inputs the optical beam 118 into four separate fiber optic cables 120a, 120b, 120c and 120d. The first fiber optic cable 120a interfaces with the power tracking device 110 which functions to track the changing power of the optical beam 118 emitted from tunable laser 106. The second and third fiber optic cables 120b and 120c interface with the wavelength tracking device 112 which functions to track the changing wavelengths of the optical beam 118 emitted from the tunable laser 106. The fourth fiber optic cable 120d interfaces with the imaging system 114 which illuminates and images a predetermined number of the biosensors 102 which in this example are located within the wells of the microplate 104. For a detailed discussion about an exemplary microplate 104, reference is made to the co-assigned U.S. patent application Ser. No. 11/489,173 (the contents of which are incorporated by reference herein).

As shown, the imaging system 114 includes illumination optics 122, imaging optics 124 (e.g., telecentric lens 138), and a 2-D imaging device 126 (e.g., a charge coupled device (CCD) camera 126, a complementary metal oxide semiconductor (CMOS) camera 126). Basically, the illumination optics 122 convert the optical beam 118 into one or more interrogation beams 128 which illuminate one or more biosensors 102 (in this example one interrogation beam 128 is shown illuminating multiple biosensors 102 which are located in the microplate 104). The imaging optics 124 collect an image 129 from the illuminated biosensor(s) 102. And, the 2-D imaging device 126 obtain a sequence of the collected images 129 each of which corresponds with one of the distinct wavelengths of the optical beam 118 that is emitted from the tunable laser 106. In particular, the 2-D imaging device 126 takes a sequence of pictures of the illuminated biosensor(s) 102 where each image 129 corresponds with one of the distinct wavelengths of the optical beam 118 that is emitted from the tunable laser 106. Lastly, the data processing device 116 (e.g., computer 116, microprocessor 116, field programmable gate array (FPGA) 116) receives the collected images 129 and processes the collected images to determine for example whether or not there was a biochemical interaction or other event on one or more of the biosensors 102.

Examples of four exemplary imaging systems 114 and how those imaging systems 114 function are discussed next with respect to FIGS. 1-4. In FIG. 1, the imaging system 114 shown has a near normal incident angle at about 2 degrees where the illumination optics 122 include a lens 130 which receives the optical beam 118 and outputs an interrogation beam 128 towards a collimating lens 132. The collimating lens 132 collimates the received interrogation beam 128 and directs the collimated interrogation beam 128 towards a mirror/reflector 134. The mirror/reflector 134 reflects the collimated interrogation beam 128 which travels through a beam splitter 136 and illuminates a predetermined number of biosensors 102 located within the wells of the microplate 104. Alternatively, the illumination optics 122 can be configured to convert the received optical beam 118 into multiple interrogation beams 128 where each interrogation beam 128 would illuminate a corresponding biosensor 102 located within a well of the microplate 104. In addition, the imaging system 114 has a telecentric lens 138 which has a field of view that was specifically selected to collect an image 129 from the illuminated biosensor(s) 102. Lastly, the imaging system 114 has a 2-D imaging device 126 (attached to the telecentric lens 138) which takes/collects a sequence of pictures/images 129 of the illuminated biosensor(s) 102 (note: each picture/image 129 corresponds with a different wavelength of the optical beam 118/interrogation beam 128).

Figure 2:
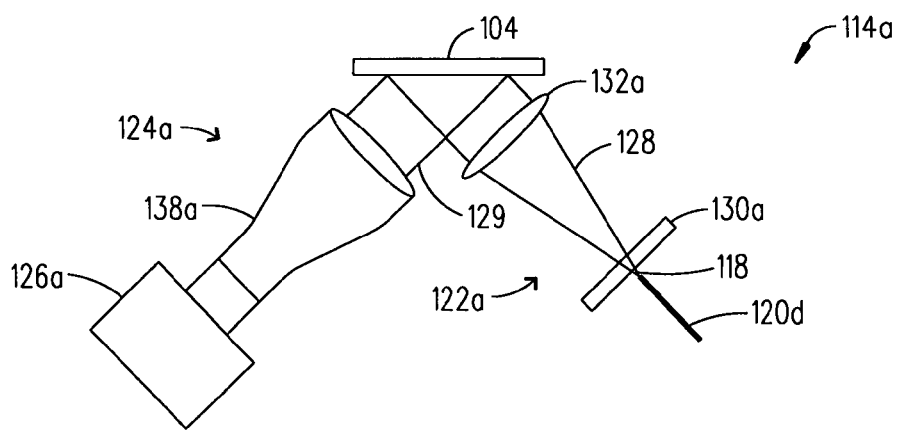
FIGS. 2-4 are block diagrams of three exemplary imaging systems that can be incorporated within the swept wavelength imaging optical interrogation system in accordance with the present invention.

Referring to FIG. 2, there is an exemplary imaging system 114a shown which has an oblique incidence configuration in accordance with another embodiment of the present invention (note: the oblique incidence angle eliminates the need for a beam splitter 136 and can improve the optical efficiency by a factor of 4). In this embodiment, the imaging system 114a has illumination optics 122a including a lens optic 130a which receives the optical beam 118 and outputs an interrogation beam 128 at a predetermined angle towards a collimating lens 132a. The collimating lens 132a receives the interrogation beam 128 and outputs the collimated interrogation beam 128 which illuminates a predetermined number of biosensors 102 located within the wells of the microplate 104. Alternatively, the illumination optics 122a can be configured to convert the received optical beam 118 into multiple interrogation beams 128 where each interrogation beam 128 would illuminate a corresponding biosensor 102 located within the well of the microplate 104. In addition, the imaging system 114a has a telecentric lens 138a which is positioned at a predetermined angle and has a field of view that was specifically selected to collect an image 129 from the illuminated biosensor(s) 102. Lastly, the imaging system 114a has 2-D imaging device 126a (attached to the telecentric lens 138a) which takes/collects a sequence of pictures/images 129 of the illuminated biosensor(s) 102 (note: each picture/image 129 corresponds with a different wavelength of the optical beam 118/interrogation beam 128).

Figure 3:
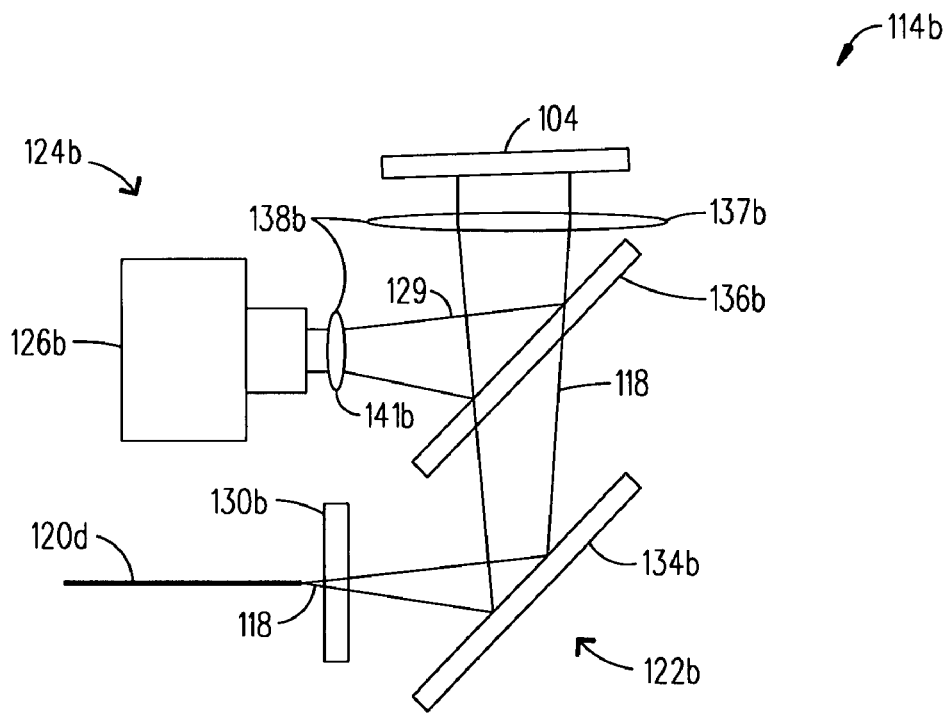

Referring to FIG. 3, there is an exemplary imaging system 114b shown which has a relatively small footprint because the illumination optics 122b and the imaging optics 124b share a front lens (or lens group) 137b of the telecentric lens 138b in accordance with another embodiment of the present invention. In this embodiment, the imaging system 114b has illumination optics 122b including a lens 130b which receives the optical beam 118 and outputs an interrogation beam 128 towards a mirror/reflector 134b. The mirror/reflector 134b reflects the interrogation beam 128 which travels through a beam splitter 136b towards the front lens (or lens group) 137b of the telecentric lens 138b. The front lens (or lens group) 137b outputs the interrogation beam 128 which illuminates a predetermined number of biosensors 102 located within the wells of the microplate 104. The front lens (or lens group) 137b also collects an image 129 from the illuminated biosensor(s) 102 and directs the collected image 129 towards the beam splitter 136b. The beam splitter 136b reflects the collected image 129 towards a back lens 141b of the telecentric lens 138b. Thus, the back lens 141b receives the collected image 129 from the illuminated biosensor(s) 102 via the front lens (or lens group) 137b and the beam splitter 136b. Lastly, the imaging system 114b includes a 2-D imaging device 126b (attached to the back lens 141b of the telecentric lens 138b) which takes/collects a sequence of pictures/images 129 of the illuminated biosensor(s) 102 (note: each picture/image 129 corresponds with a different wavelength of the optical beam 118/interrogation beam 128).

Figure 4:
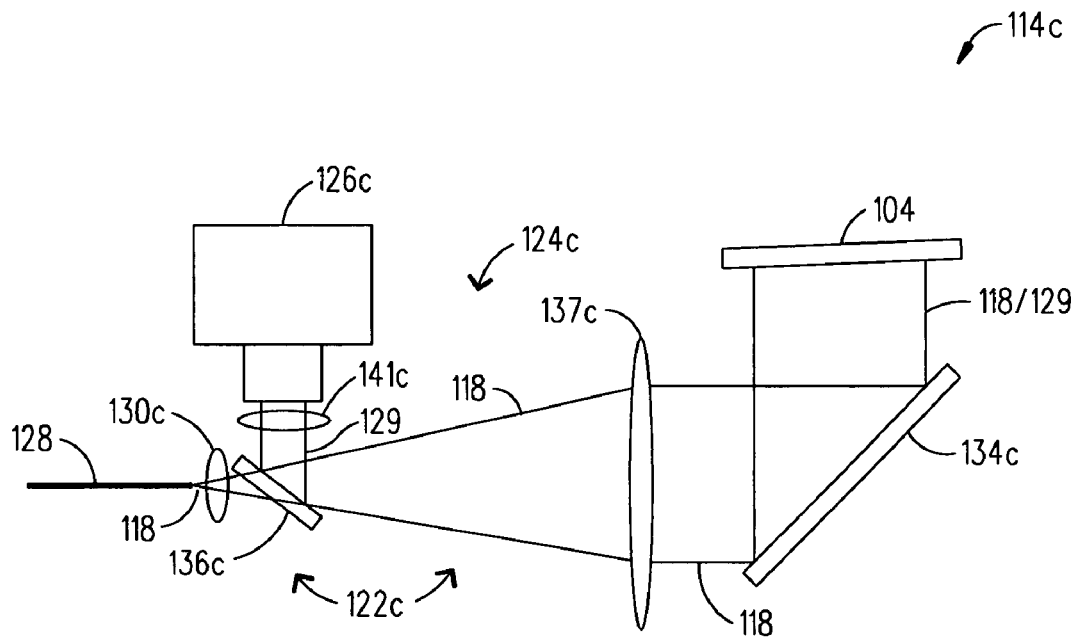

Referring to FIG. 4, there is an exemplary imaging system 114c where the illumination optics 122c and the imaging optics 124c share a front lens (or lens group) 137c of the telecentric lens 138c in accordance with another embodiment of the present invention. In this embodiment, the imaging system 114c has illumination optics 122c including a lens 130c which receives the optical beam 118 and outputs an interrogation beam 128 through a beam splitter 136c towards the front lens 137c of the telecentric lens 138c. The front lens 137c of the telecentric lens 138c collimates the interrogation beam 128 and directs the collimated interrogation beam 128 to a mirror/reflector 134c. The mirror/reflector 134c reflects the interrogation beam 128 so the reflected interrogation beam 128 can illuminate a predetermined number of biosensor(s) 102 located within the wells of the microplate 104. The mirror/reflector 134c also receives an image 129 of the illuminated biosensor(s) 102 and directs the image 129 through the front lens 137c of the telecentric lens 138c and off the beam splitter 136c to the back lens (or lens group) 141c of the telecentric lens 138c. The back lens (or lens group) 141c directs the collected image 129 towards the 2-D imaging device 126c. Then, the 2-D imaging device 126b (attached to the back lens 141b of the telecentric lens 138b) takes/collects a sequence of pictures/images 129 of the illuminated biosensor(s) 102 (note: each picture/image 129 corresponds with a different wavelength of the optical beam 118/interrogation beam 128).

A detailed discussion is provided next about components 106, 110, 112, 116, 122, 124 and 126 which a part of the optical interrogation system 100. Then, a detailed discussion is provided about one experiment where an optical interrogation system 100 was used to interrogate a single biosensor 102 located within a well of a 96-well microplate 104. Next, a detailed discussion is provided about another experiment where an optical interrogation system 100 was used to interrogate many biosensors 102 located within the wells of a 384-well microplate 104. Thereafter, a detailed discussion is provided to discuss some additional features and capabilities associated with the optical interrogation system 100.

Tunable Laser 106

The preferred tunable laser 106 is a semiconductor diode laser based swept wavelength tunable laser. In one example, the swept wavelength tunable laser 106 can be tuned over a tuning range from 838 nm to 853 nm without mode hop and have a tuning speed in the range of 0.1 nm/sec to 300 nm/sec. The preferred swept wavelength tunable laser 106 also has a fiber coupled optical power of about 5 mW over the tuning range. In addition, the preferred swept wavelength tunable laser 106 has a wavelength interrogation range of less than 10 nm which is appropriate in label-free interrogation since the resonance spectral width of a WGC biosensor 102 is typically designed to be about 1 nm.

Power Tracking Device 110

The power tracking device 110 tracks the changing power of the optical beam 118 emitted from the tunable laser 106 (note: the power of the tunable laser 106 varies as it changes the wavelength of the optical beam 118). The power tracking device 110 monitors this changing power which is used by the data processing device 116 as a power reference to remove the effect of power variations in the output of the spectra from the interrogated biosensor(s) 102.

Wavelength Tracking Device 112

The wavelength tracking device 112 functions to track the changing wavelengths of the optical beam 118 emitted from the tunable laser 106. In one embodiment, the wavelength tracking device 112 includes a fiber Mach-Zehnder interferometer 140 and an athermalized etalon 142. The fiber Mach-Zehnder interferometer 140 is used to decode the instantaneous laser wavelength to a very high resolution while operating the tunable laser 106. The athermalized etalon 142 is used to provide an accurate reference of the laser wavelength while operating the tunable laser 106. For instance, the fiber Mach-Zehnder interferometer 140 can have a free spectral range (FSR) of 4 pm. And, the athermalized etalon 142 can have a FSR of 200 pm and a finesse of 100.

Another way one can use to track the changing wavelengths of the optical beam 118 emitted from the tunable laser 106 is to place a dispersive element into the optical path of the interrogation beam 128 such as at a grating in or near one of the biosensors 102 and then use a predefined area of the 2-D imaging device 126 to detect and monitor the laser's wavelength. For instance, this solution may be implemented by using a grating coupled waveguide with a chirped period in the vicinity of one of the biosensors 102. This grating coupled waveguide would be illuminated by the same collimated illumination beam 128 as the other biosensors 102. Because this grating coupled waveguide has a chirped period, the light 128 will not be reflected except at some specific locations where the local period of the grating coupled waveguide and the wavelength of the tunable laser 106 are such that the resonance condition is matched (see the following equation):

$$\lambda = \Lambda(x)(N_{eff} +/- \sin(\theta))$$

Where $\lambda$ is the wavelength of the tunable light laser 106;

$\Lambda(x)$ is the local period of the grating in the grating coupled waveguide;

Neff is the effective index of the grating coupled waveguide;

$\theta$ is the incidence angle of the interrogating collimated beam 128.

In this equation, the period of the grating is a function of the position along the grating coupled waveguide. So, a variation of the wavelength will change the position of the resonnance in the x direction. And, by imaging that grating on the same 2-D imaging device 126 as the one used for the measurement, one can also measure the position of the resonnance and, thus monitor the wavelength of the tunable light source 106.

Illumination Optics 122

The illumination optics 122 typically generate an interrogation beam 128 which is preferably uniform and has a flat wavefront to match the flat bottom of the microplate 104. If the bottom surface of the microplate 104 is slightly curved, then the illuminating optics 122 can adjust the collimated wave front of the interrogation beam 128 to conform to the curved bottom surface of the microplate 104. Alternatively, the illumination optics 122 can generate multiple parallel interrogation beams 128 with smaller sizes that can be used to illuminate individual biosensors 102. In either case, the incident angle of the interrogation beam(s) 128 is chosen such that the grating resonance wavelength of the biosensor(s) 102 is within the tuning range of the tunable laser 106.

As shown in FIGS. 1-4, the interrogative beam 128 may be generated by using a lens 132 (for example) to collimate the optical beam 118 output from the delivery fiber 120d. If desired, the lenses 132 can by replaced by curved surface reflective mirrors. In addition, the size of the interrogation beam 128 is matched to the field of view of the imaging optics 124 and the pixel size of the focal plane of the 2-D imaging device 126. The imaging area can be the size of an entire microplate 104, a partial area of a microplate 104, a microscope slide, a sensor chip etc. . . .

Imaging Optics 124

The imaging optics 124 collect an image from the illuminated biosensor(s) 102. For instance, the imaging optics 124 can be a standard machine vision telecentric lens 138 like ones made by Edmund Industrial Optics or Opto-Engineering (see FIG. 1). The field of view of the telecentric lens 138 is normally selected depending on the particular area of interest (i.e., number of biosensors 102 to be interrogated in the microplate 104).

2-D Imaging Device 126

The 2-D imaging device 126 (attached to the telecentric lens 138) takes/collects a sequence of pictures/images 129 of the illuminated biosensor(s) 102. In particular, the 2-D imaging device 126 takes a sequence of pictures 129 of the illuminated biosensor(s) 102 where each picture 129 corresponds with one of the distinct wavelengths of the optical beam 118 (interrogation beam 128) that is emitted from the tunable laser 106. In one example, the 2-D imaging device 126 can be a CMOS or a CCD camera with a 2-D focal plane imaging array and a global shutter which enables the entire imaging array to be exposed simultaneously. The 2-D imaging device 126 is typically controlled by an external trigger signal wherein when the tunable laser 106 scans across the tuning range, the camera 126 takes a sequence of spectral images 129 with each spectral image 129 corresponding to one of the wavelengths of the tunable laser 106. The collection of spectral images 129 form a "data cube" as illustrated in FIG. 5 (note: in the "data cube" the particular wavelength of the tunable laser 106 is encoded by the timing of each spectral image 129 and each spectral imaging pixel contains an interrogated sensor spectrum).

Data Processing Device 116

The data processing device 116 (e.g., computer 116, microprocessor 116, FPGA 116) receives the collected images 129 ("data cube") and uses image processing software and digital filters to automatically process the collected images ("data cube") to (for example): (1) determine whether or not there was a biochemical interaction or other event on one or more of the illuminated biosensor(s) 102; (2) locate sensor region(s) and/or reference region(s) on each of the illuminated biosensor(s) 102; (3) remove defect regions on each of the illuminated biosensor(s) 102; and/or (4) calibrate a uniformity of surface chemistry and target molecule immobilizations on each of the illuminated biosensor(s) 102 (note: the coherent interference from optical interfaces can be removed by using digital filters). If desired, the data processing device 116 can bin together multiple imaging regions (pixels) with prior knowledge about for example the locations of the sensor regions and reference regions on the biosensors 102. In this mode, multiple pixels are grouped together as a singe detector and the number of sensor spectra/images is reduced to the number of binned regions. In this way, the data processing can be greatly simplified.

Figure 5:
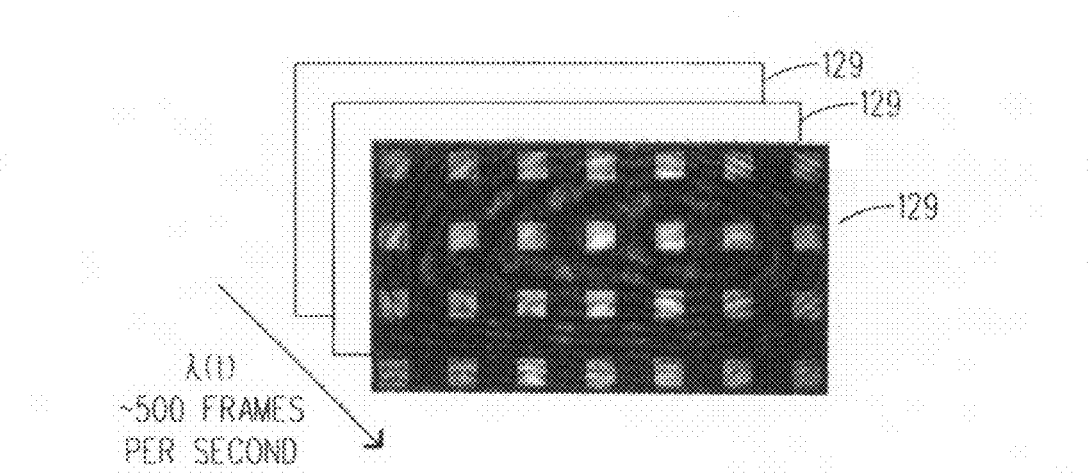
FIG. 5 is a diagram of a "data cube" which is generated by the swept wavelength imaging optical interrogation system after interrogating two biosensors in accordance with the present invention.
Figure 6A:
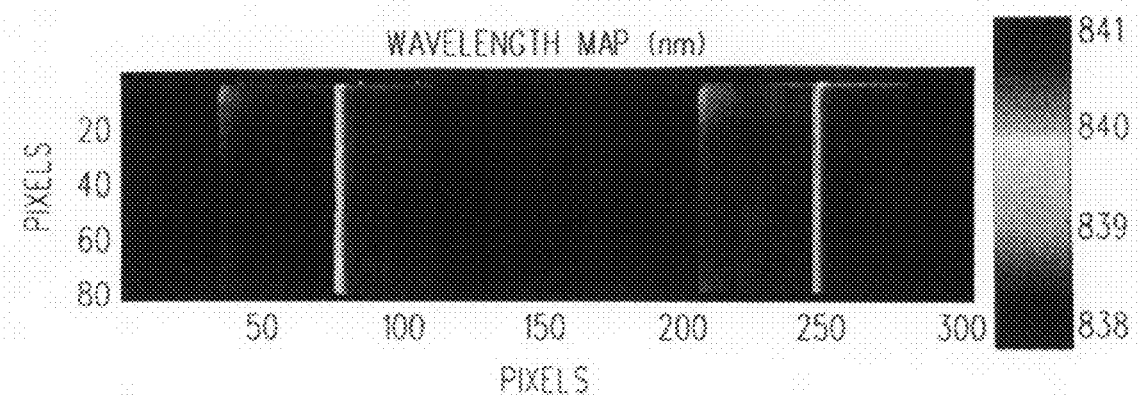
FIGS. 6A and 6B are respectively images of a centroid wavelength map and an amplitude map that where obtained by the swept wavelength imaging optical interrogation system after processing the "data cube" in accordance with the present invention.
Figure 6B:
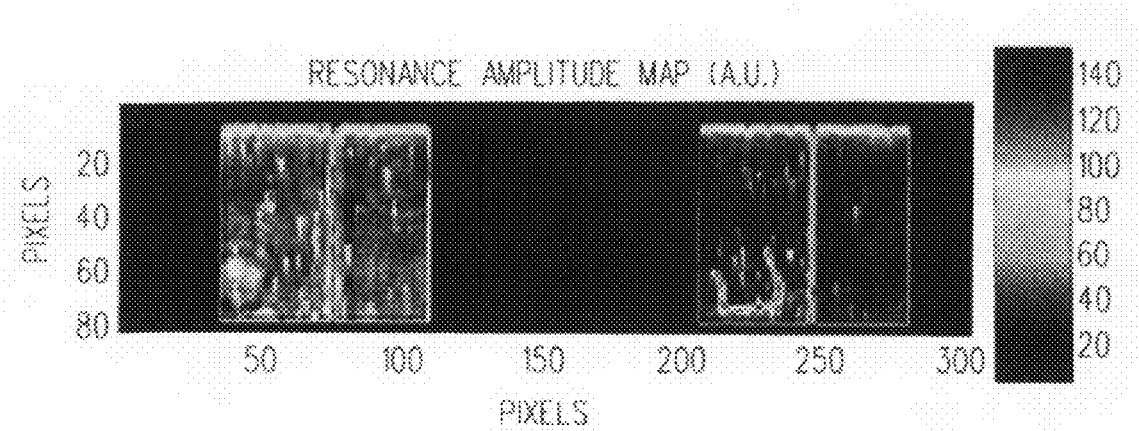

In one experiment, the data processing device 116 processed the "data cube" shown in FIG. 5 which was associated with two biosensors 102 and generated a centroid wavelength map (FIG. 6A) and an amplitude map (FIG. 6B) (note: the imaging regions were not binned in this example). Each of these biosensors 102 had half of it's surface coated with a thick waveguide and the other half of it's surface coated with a normal waveguide. Plus, the wells in the microplate 104 in which the biosensors 102 where located were filled with water. The x axis and the y axis in both of the 2-D maps correspond with the array of pixels in the 2-D camera 126 and each pixel contains a spectrum where the centroid wavelength and the peak amplitude of all of those spectrums are shown in the 2-D maps. In these maps, it can be seen that the resulting resonant wavelengths of both biosensors 102 differed by about 3 nm. As can be appreciated, this 2-D mapping process which is used to identify the responses for each biosensor 102 involves using a massive amount of parallel processing operations.

If one wanted to achieve a data rate of 1 Hz for a specific interrogation application, then the sequential scanning of the tunable laser 106 and the sequential acquisition of all the spectral images 129 by the 2-D imaging device 126 would need to be completed in 1 second. This requirement is well within the current capability of the commercially available tunable lasers 106. Of course, to meet this capability or any other data rate for that matter it should be appreciated that the number of desired wavelength sampling points is going to dictate the frame rate of the 2-D imaging device 126. For example, if one wants to obtain 500 wavelength samples during a single tuning sequence then the camera frame rate needs to be as fast as 500 frames per second. A CMOS camera 126 such as the Basler A504k is able to deliver 500 fps at a full 1024×1208 pixel format (note: a higher frame rate is possible if one obtained a partial image area). In an application where it is not necessary to achieve a 1 Hz data rate, then a slower camera 126 could be used instead such as a CCD camera or a less expensive CMOS camera.

The data processing device 116 is going to have to process a great deal of data when using binned-based image processing and even more data when using pixel-based image processing. One type of data processing device 116 that can be used to process this amount of data is a field programmable gate array (FPGA) which is able to perform massively parallel logic operations. In fact, the FPGA 116 can be used to perform the pixel binning, spectral filtering, digital filtering and the 2-D image processing including centroid computation (where the centroid wavelength for each pixel is obtained) If desired, the FPGA 116 can also be directly embedded into the 2-D imaging device 126.

Exemplary Optical Interrogation System 100

An optical interrogation system 100 has been made and tested which had a configuration as illustrated FIG. 1. The optical interrogation system 100 included a wavelength tracking device 112 which used a fiber Mach-Zehnder interferometer 140 and an athermalized etalon 142 for real time tracking of the transient laser wavelength. In this set-up, the Mach-Zehnder interferometer 140 and etalon 142 outputs were fed into an analog to digital data acquisition (DAQ) card (in particular a NI PCI 1643), which has a simultaneous sampling rate of up to 250 kS/s with a 16 bit resolution. A Basler A504k high speed CMOS camera 126 along with a NI PCIe-1429 frame grabber (not shown) where used in the optical interrogation system 100. The Basler A504K CMOS camera 126 operated at 1000 fps when the region of interest was set to 750×500 pixels. And, the frame grabber streamed the image data from the CMOS camera 126 directly into the computer 116.

Figure 7:
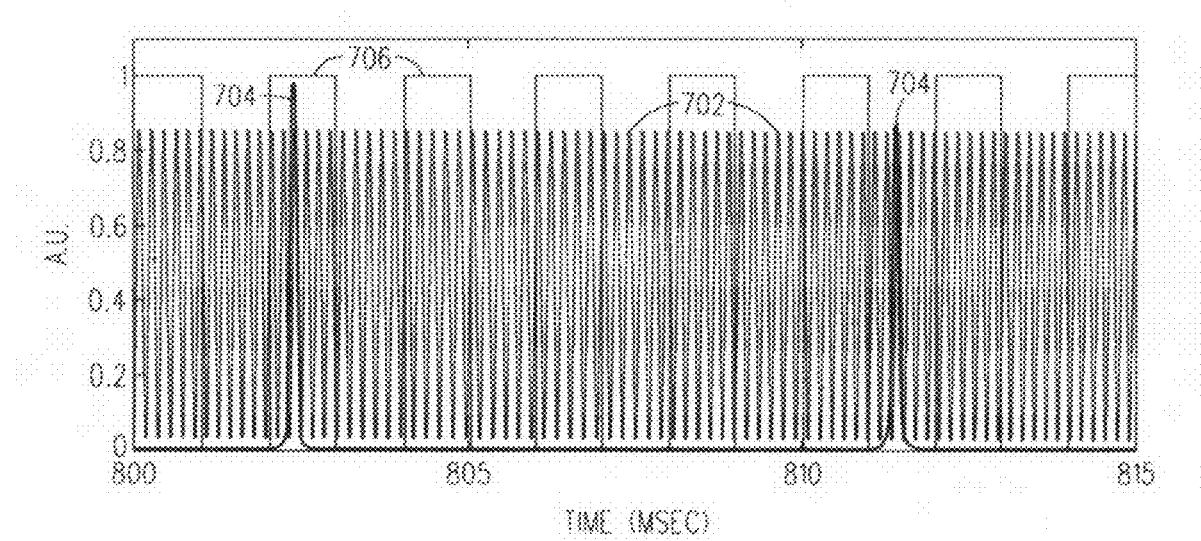
FIG. 7 is a graph which is used to help explain the triggering of a 2-D camera that is located within in an exemplary swept wavelength imaging optical interrogation system in accordance with the present invention.

In this set-up, the frame grabber was connected to the DAQ board (associated with the wavelength tracking device 112) via a real-time system integration (RTSI) bus, and the CMOS camera 126 was set to operate in an external trigger mode. The multi-function DAQ card was also used to generate triggering pulses through one of its counter outputs. These trigger pulses which where routed through the RTSI bus were used trigger the CMOS camera 126/frame grabber board. Thus, the CMOS camera 126 had a frame rate which was programmatically adjustable by controlling the DAQ card's triggering pulses. As such, when the tunable laser 106 started to scan, the Mach-Zehnder interferometer 140 outputs, the etalon 142 outputs where simultaneously acquired and used to trigger the CMOS camera 126. FIG. 7 is a graph which shows experimental data where the analog outputs 702 and 704 respectively from the Mach-Zehnder interferometer 140 and the etalon 142 were simultaneously acquired as well as showing the camera's triggering pulses 706. The camera 126 was triggered by the rising edges of the counter pulses 706. In this example, a fringe counting algorithm was used to determine the tunable laser's wavelength as a function of time. In this way, the timing of each image 129 could then be used to compute the average wavelength of each image 129. After locating the wavelength of each frame, each pixel or pixel group could then be processed in a manner where the sensor spectra undergoes digital filtering to remove parasitic interference fringes before the final computation of centroid wavelengths. An example of this type of processing was discussed in a co-assigned U.S. Patent Application No. 60/781,397 filed on Mar. 10, 2006 and entitled "Optimized Method for LID Biosensor Resonance Detection". The contents of this document are hereby incorporated by reference herein.

In this experiment, the data acquisition time was typically 1 second while the CMOS camera 126 operated at 500 fps. The computer 116 generated a stack of images 129 which formed a "data cube" (e.g., see FIG. 5). The computer 116 can use two different approaches to processes the "data cube". The first approach is based on pixel binning, by which multiple regions-of-interest (ROIs) are created in software and then the pixels are averaged in each ROI to form a channel. For instance, in a full plate measurement system, 768 ROIs are generated where two ROIs were created for each well which contained a biosensor 102 with a reference region and a sample region. For a detailed discussed about this particular type of biosensor 102, reference is made to co-assigned U.S. patent application Ser. No. 10/027,509 filed on Dec. 29, 2004 and entitled "Method for Creating a Reference Region and a Sample Region on a Biosensor and the Resulting Biosensor". The contents of this document are hereby incorporated by reference herein.

The second approach is to treat each pixel as a sensing channel which is label-free imaging in the real sense but can be computationally intensive for the computer 116. In this approach, the computer 116 may need to save the image data and process it off-line. However, a discussion is provided later to describe different ways to achieve <1 second data processing time.

Single Well—Optical Interrogation System 100

An optical interrogation system 100 was used to interrogate a single biosensor 102 located within a well of a 96-well microplate 104 in order to investigate the system noise and resolution. The imaging system 114 had two_near infrared (NIR) achromats where the focal lengths of the lenses were 200 mm and 100 mm, respectively. This lens set formed a 2× imaging system 114. And, one pixel in the image plane corresponded to 6 μm in the object space of the Basler A504k camera 126. A fiber collimator was built using a 75 mm focal length lens_132. This particular optical interrogation system 100 was designed to have a field of view of 3×3 mm$^2$ which is the size of a single grating biosensor 102 located within a well of a 96-well microplate 104. If desired, the optical interrogation system 100 could also be flexibly configured to measure an entire 96-well, 384-well or 1536-well microplate 104 using either TM or TE interrogations.

Figure 8A:
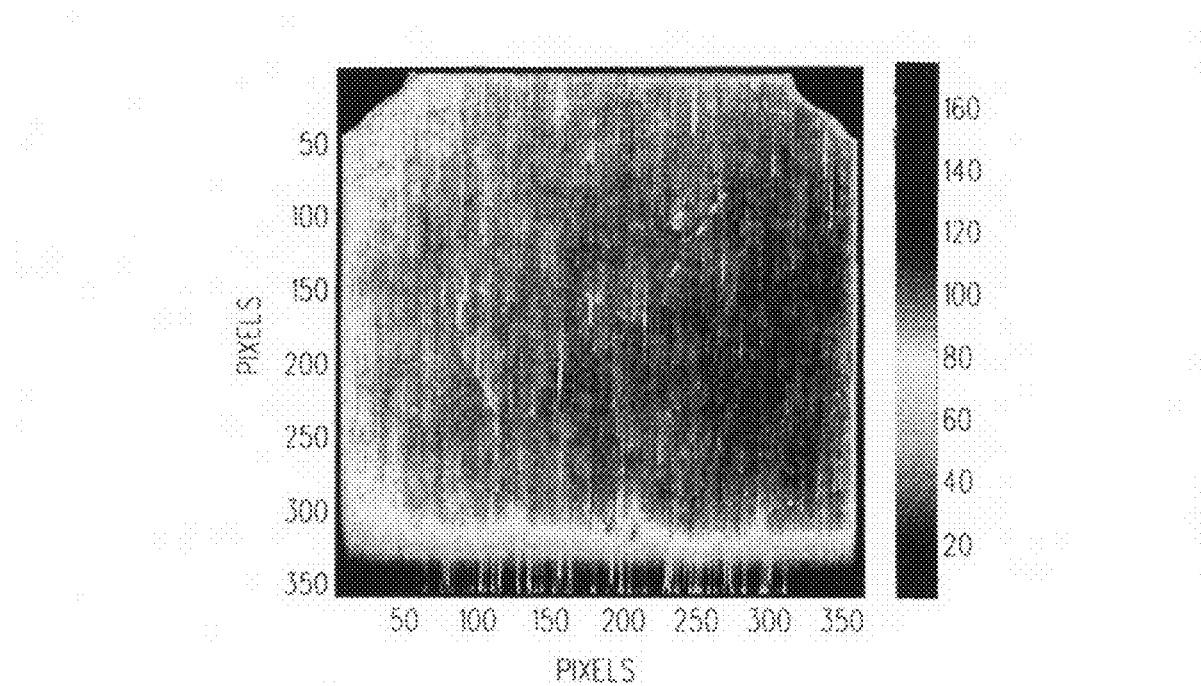
FIGS. 8-11 are various images and graphs which were obtained after an exemplary swept wavelength imaging optical interrogation system interrogated a single biosensor located in a microplate in accordance with the present invention.
Figure 8B:
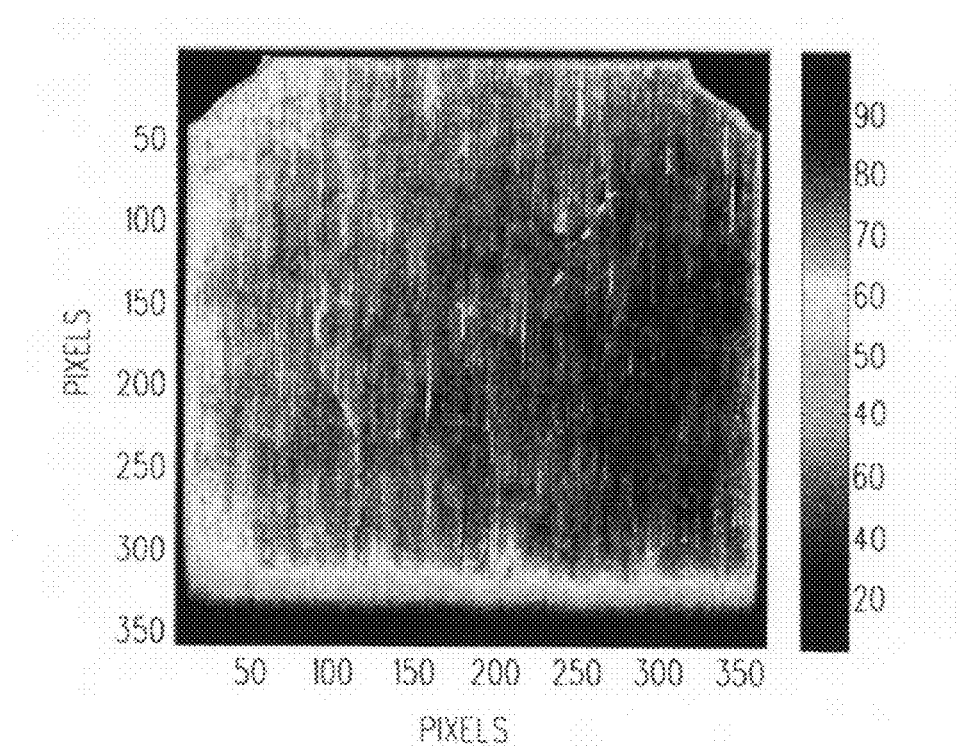

In this experiment, the optical interrogation system 100 used a tunable laser 106 with a 10 nm tuning range and a Basler A504k camera 126 which was set to take one set of images at 500 fps which enabled the data acquisition to be completed in 1 second. The computer 116 used pixel-based processing to process the acquired "data cube" to determine a resonance wavelength and a resonance amplitude. The amplitude maps of a biosensor 102 in a well filled with water are shown in FIGS. 8A and 8B. In FIGS. 8A and 8B, the biosensor 102 had grating defects which can be easily seen in the amplitude images. These types of grating defects are often caused by the scratches on the master, and the defect patterns tend to be repeatable from microplate to microplate. In this experiment, it was frequently observed that the bottom of the biosensor 102 had developed streak patterns at the resonant wavelength, as illustrated in the bottom portion of FIG. 8A. This effect is believed to be related to optical crosstalk. However, the blocking of the neighboring well resulted in no change. Then, it was found that when the bonding area was masked from the incident beam 128, the streaks disappeared, as can be seen in FIG. 8B. These observations suggested that the scattered light from the epoxy regions on the microplate 104 can couple into the waveguide of the biosensor 102. This guided wave is then resonantly coupled out of the grating, forming the streaks, the length of which is consistent with the coupling length of leaky waves. The coupling distance was measured to be about 216 μm.

Figure 9A:
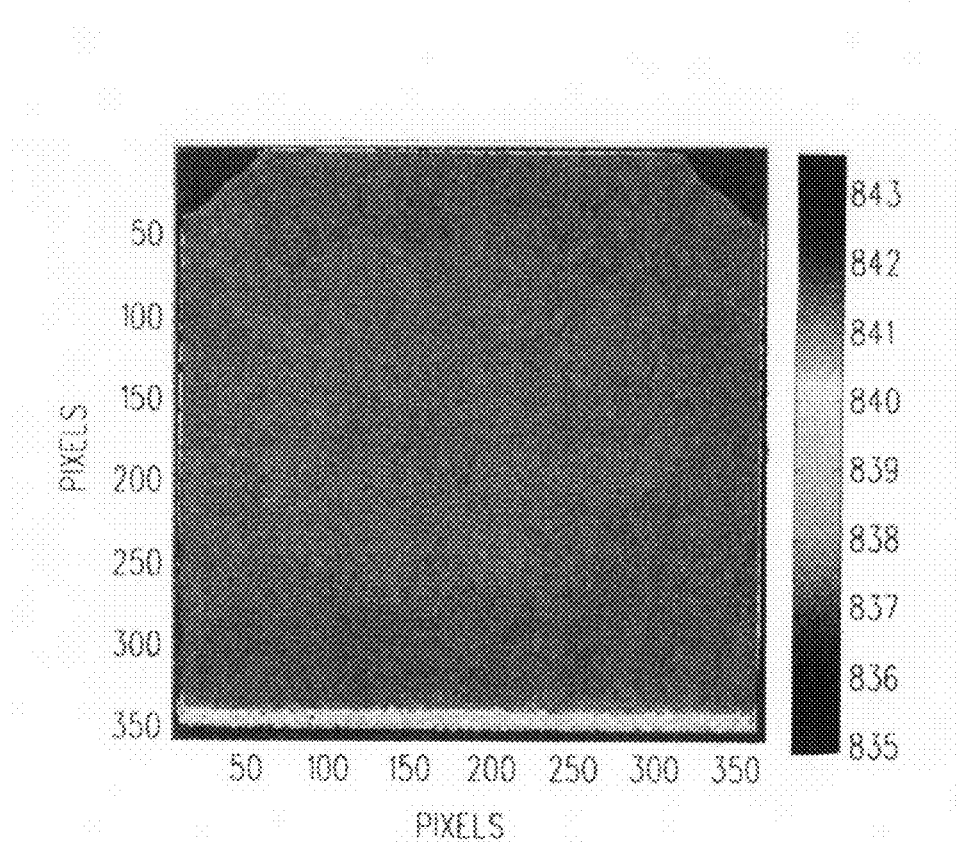
Figure 9B:
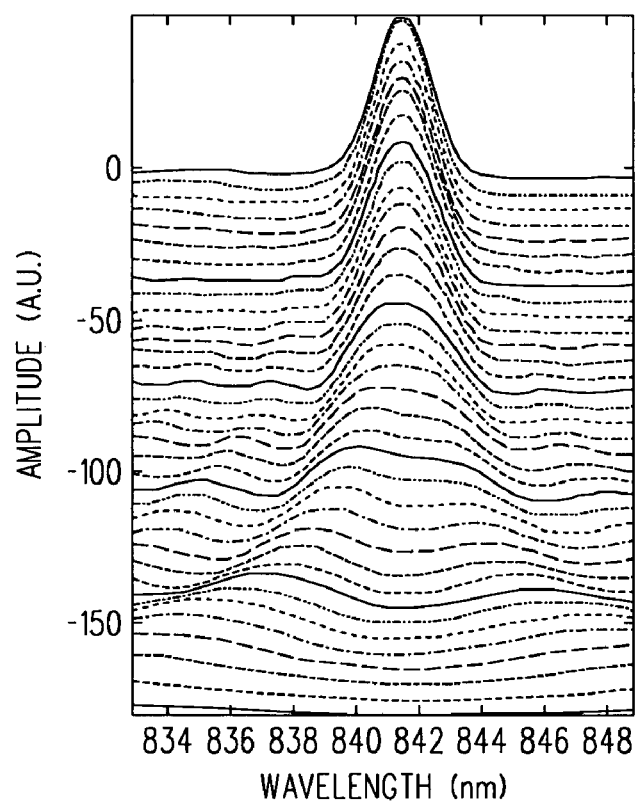

To gain further insight into the physics associated with the coupling distance from the grating edge of the biosensor 102, the resonance map of the biosensor 102 was plotted and it was found to have a substantial difference of centroid wavelength in the bottom area, as depicted in FIG. 9A. This edge effect is likely to be an artifact because the evanescent wave was not fully developed in the initial 200 μm propagation distance. To confirm this hypothesis, the grating spectra was compared along the propagation direction of the evanescent wave, starting from the bottom edge of the grating in the biosensor 102. FIG. 9B is a plot of the grating spectra measured by a series of contiguous pixels along the propagation direction of the leaky wave which illustrates the continuous evolution of the grating spectrum where the lowest spectrum corresponds to the bottom edge of the biosensor 102 and the top spectrum is at 216 μm from the bottom edge of the biosensor 102. As can be seen, a well-defined resonance does not take shape until after 150 μm of propagation.

This 150 μm coupling distance limits the image resolution in the leaky wave propagation direction. In the orthogonal direction, the image resolution can approach that of a conventional microscope. This explains why these defects in the bottom of the amplitude map all appeared as streaks. To improve the resolution, the biosensor 102 can be interrogated in TE polarization, which reduces the coupling distance from 200 μm to about 20 μm. In addition, one can increase the etch depth of the grating in the biosensor 102 to further decrease the coupling distance. However, there is a trade-off in increasing the etch depth which is that the resonance becomes broadened, and the baseline noise will increase accordingly.

Figure 10:
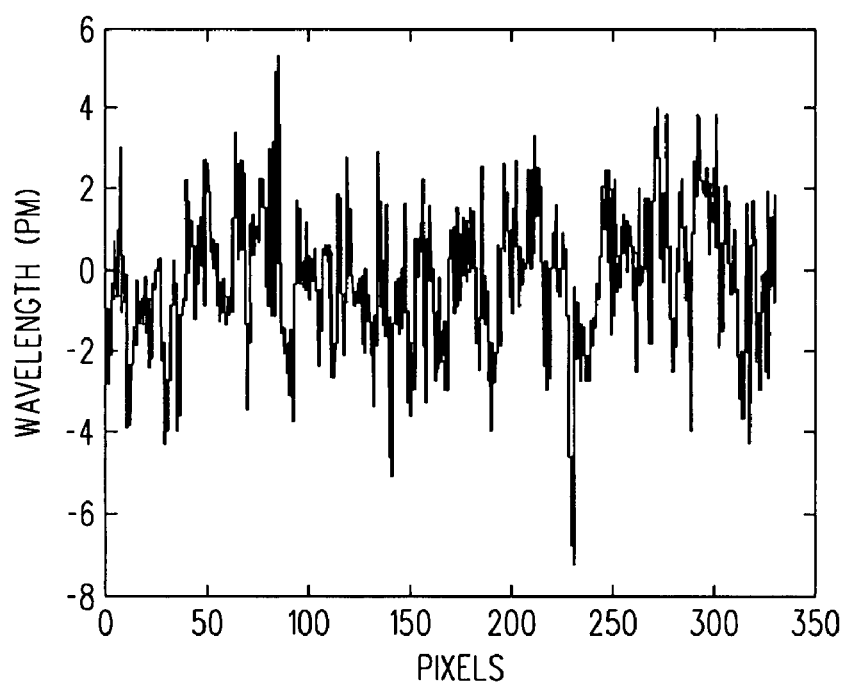

To measure the noise level in a resonant wavelength image, two sets of data were acquired at 5 minutes apart with identical conditions. The difference of the 2D resonant wavelength images of these two measurements yielded an ensemble of noise. A row of this differential wavelength image is shown in FIG. 10 and this image suggests a noise level of 1.8 pm per pixel (which corresponds to 1 pm shot noise). This result verifies the low noise performance of the Basler A504k camera 126. By comparison, the traditional photodiode non-imaging based optical interrogation system operates at about 10 times of shot noise due to the inability to closely integrate the photodiode and the amplifier electronics.

Figure 11A:
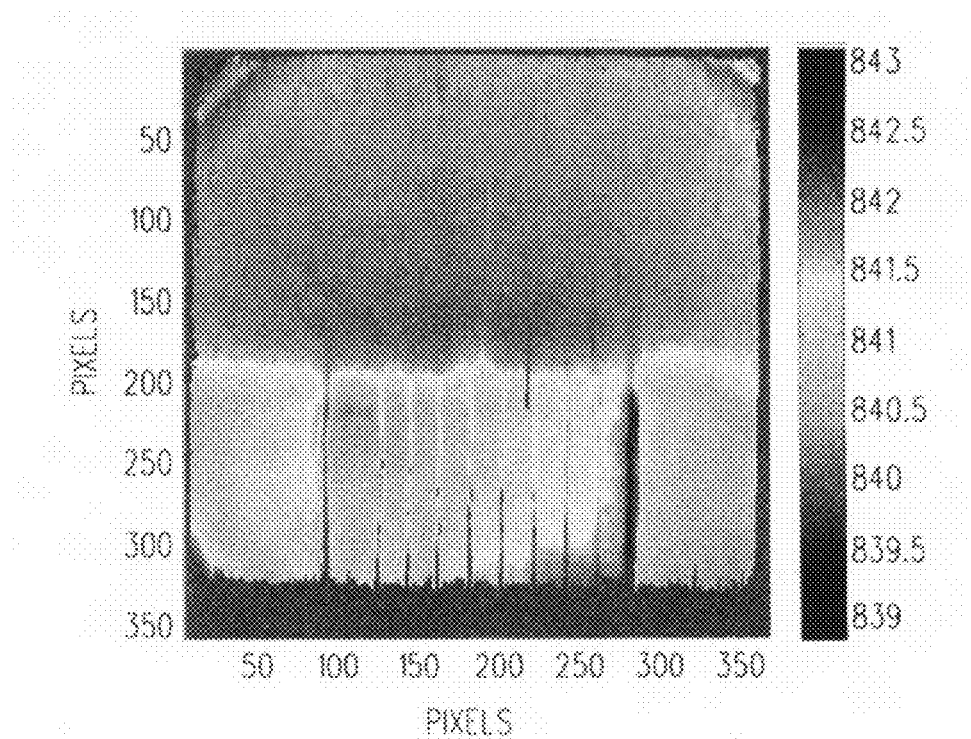
Figure 11B:
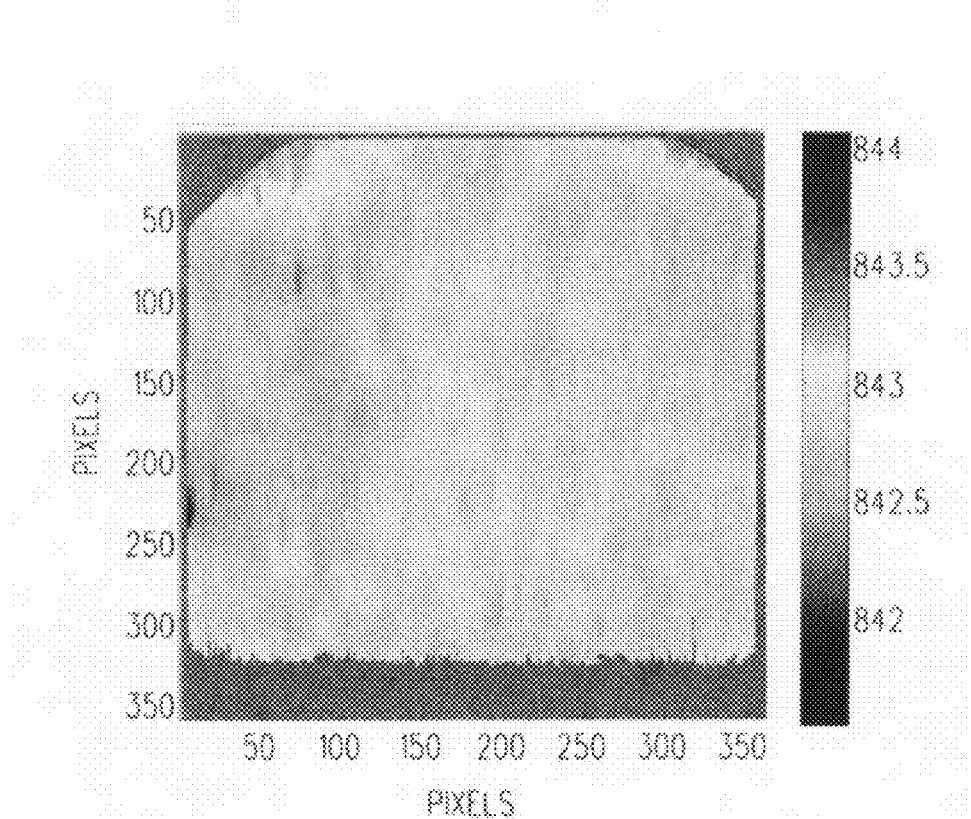

This optical interrogation system 100 was also used to interrogate a biosensor 102 which had a sample region and pin-printed reference region. FIG. 11A is an image of a wavelength map which revealed in detail the pin-printed reference region (see the bottom portion of the wavelength map). A cell assay plate with 90% confluency was also interrogated by using this optical interrogation system 100 and the resulting wavelength map is shown in FIG. 11B. Although this particular resolution was not sufficient to resolve an individual cell, the wavelength map did have good uniformity (note: the cell density appears to be higher near the edge of the well).

Full Plate—Optical Interrogation System 100

The optical interrogation system 100 used in this particular experiment to interrogate a 384-well microplate 104 was configured as shown in FIG. 1. The optical interrogation system 100 utilized a tunable laser 106 (tuning range of 10 nm), a Basler CMOS camera 126 (500 fps) and an Edmund telecentric lens 138 (0.08× magnification and 160 mm input aperture). The illumination optics 122 included a_JML Optical (JML) plano-convex lens 132 which had a 1 meter focal length and two folding mirrors 134 and 136 which could accommodate the 1 meter long focal length.

Figure 12A:
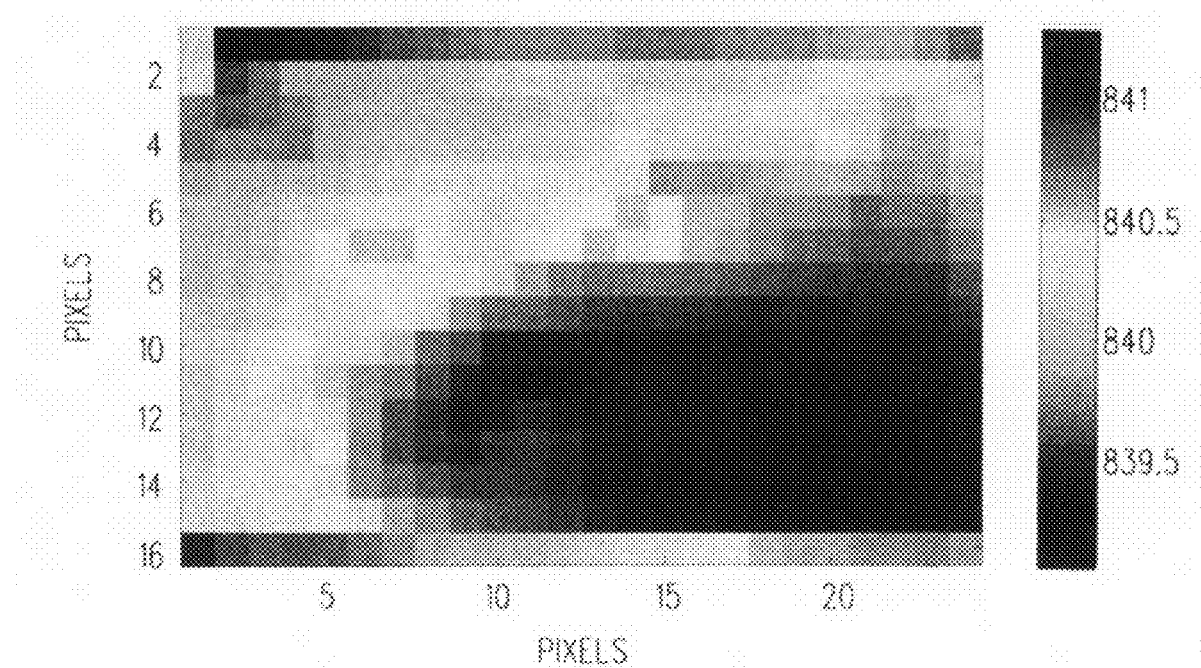
FIGS. 12-15 are various images and graphs which were obtained after an exemplary swept wavelength imaging optical interrogation system interrogated 384 biosensors located in a microplate in accordance with the present invention.
Figure 12B:
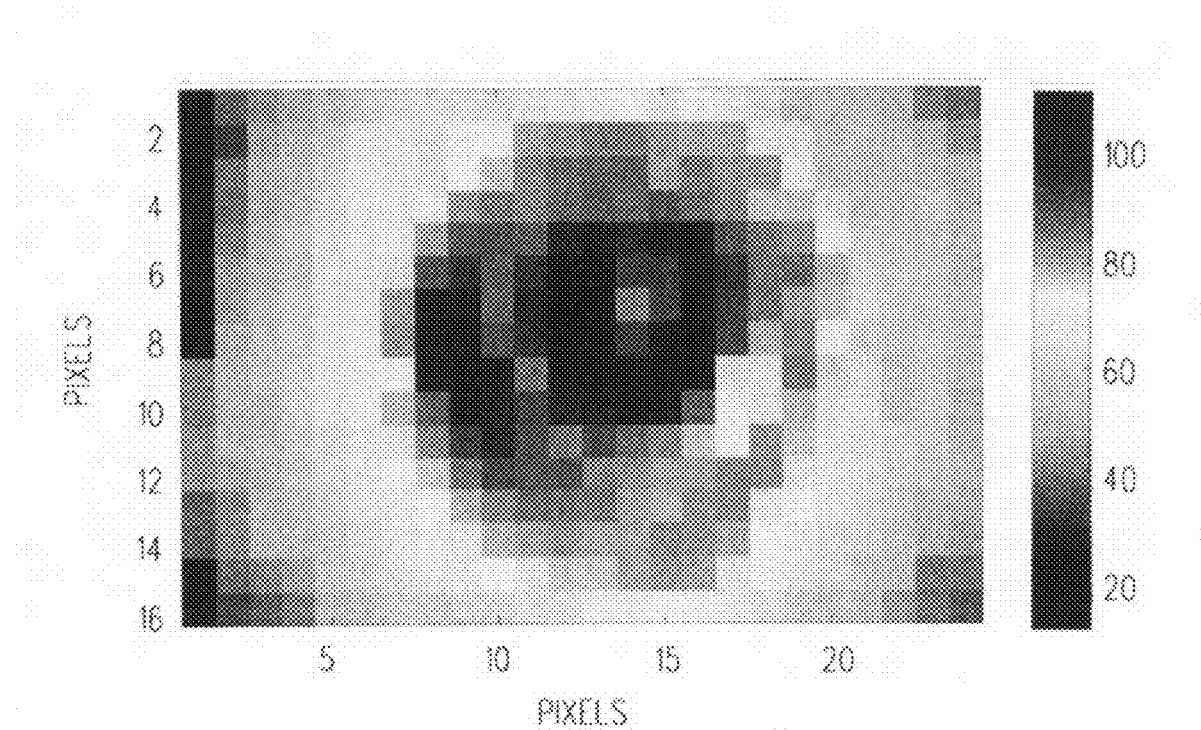

The optical interrogation system 100 had a field of view to cover the entire 384-well microplate 104 along with 768-programmatically generated regions of interest (ROIs) where each ROI corresponded to half the size of a grating ($2\times1$ mm$^2$) and used 13×6 pixels in the Basler CMOS camera 126. This particular configuration allowed in-well referencing for each of the biosensors 104 within the entire microplate 104. In this experiment, the data processing unit 116 averaged the pixels for each ROI to reduce the data processing time. A wavelength map and an amplitude map of the 384-well microplate 104 measured by this optical interrogation system 100 are respectively shown in FIGS. 12A and 12B. As can be seen in FIG. 12A, the wavelength uniformity of the microplate 104 was better than 2.5 nm. The measured amplitude distribution shown in FIG. 12B indicated that the uniformity of the optical intensity was rather poor, even though an apodizing gradient filter was used to flatten the Gaussian interrogation beam 128. The excess non-uniformity was found to be due to the angular dependence of the coating in the Edmund telecentric lens 138 (note: an Opto-Engineering telecentric lens 138 or another type of lens would likely be more suitable to use in the optical interrogation system 100).

Figure 13A:
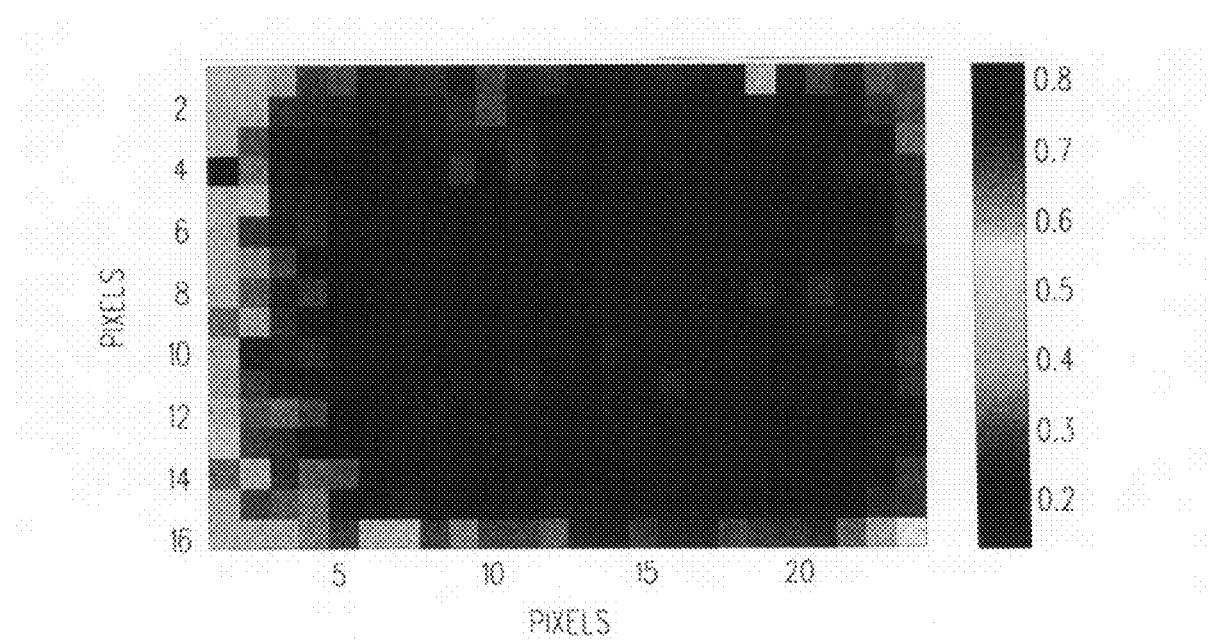
Figure 13B:
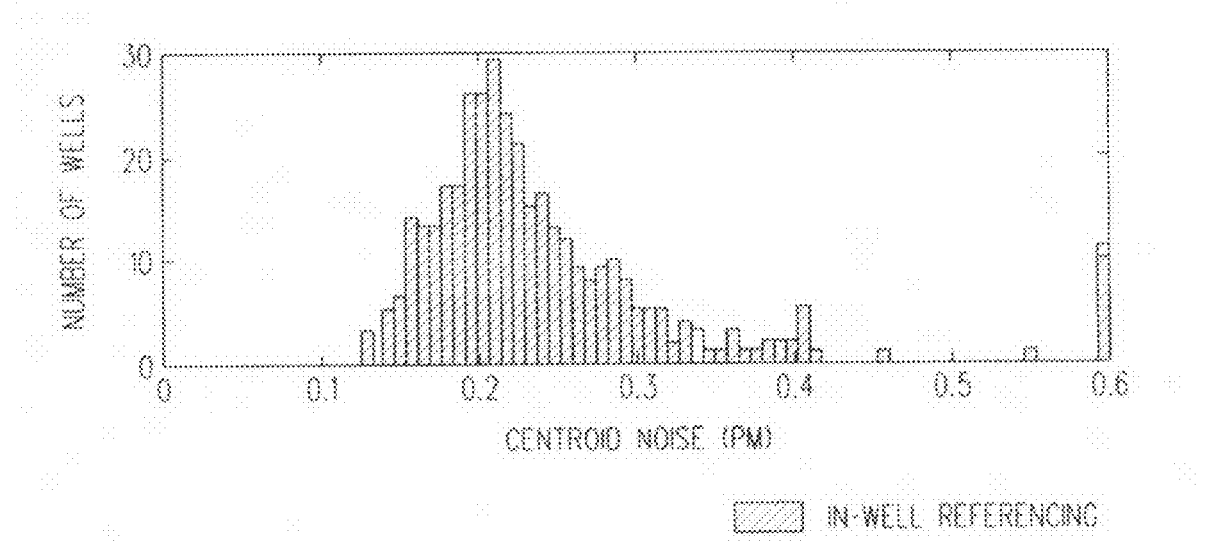
Figure 13C:
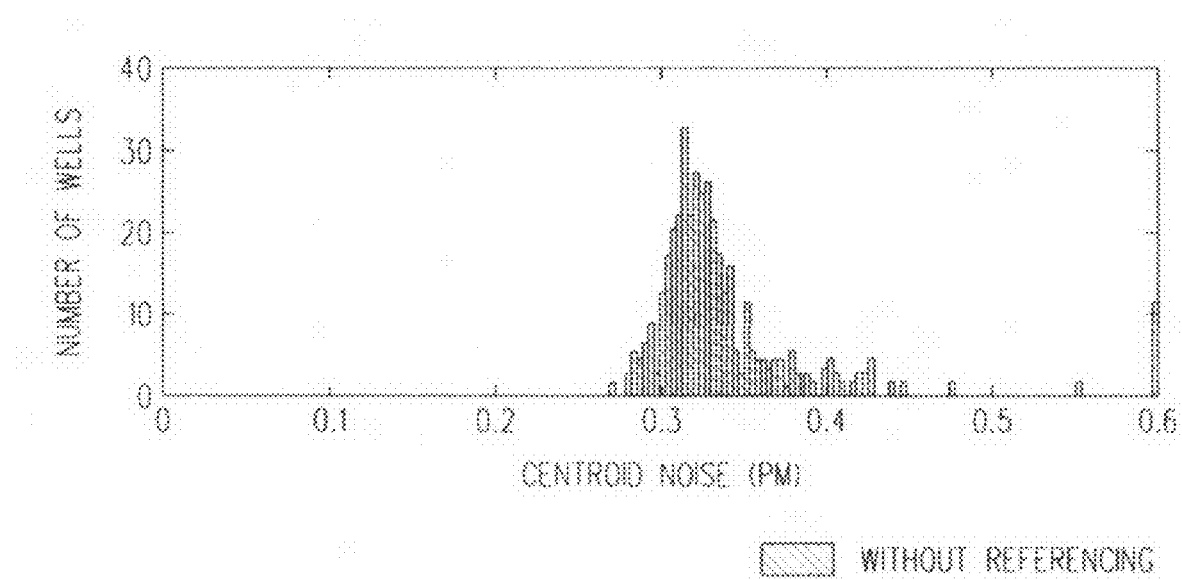

The baseline noise of this optical interrogation system 100 was also measured after making 100 continuous acquisitions. FIG. 13A shows the baseline noise which had a distribution that was well-correlated to the non-uniformity of the optical intensity, with the wells in the outer edges of the 384-well microple 104 having the higher baseline noise. FIGS. 13B and 13C are histograms which respectively illustrate the self-reference baseline noise and the non-referenced baseline noise. As can be seen, the self-referenced baseline noise is lower than that of the non-referenced baseline noise. In particular, the self-referenced baseline noise had a 0.2 pm median noise level, which is exactly equal to the single pixel noise of 1.8 pm divided by the square root of the number of pixels in the ROI. A few outliers where also present which were due to defective wells. Again, by replacing the Edmund telecentric lens 138 with the OE telecentric lens (or a similar telecentric lens) this should improve the beam uniformity such that the noise level will be lower and more consistent.

Figure 14A:
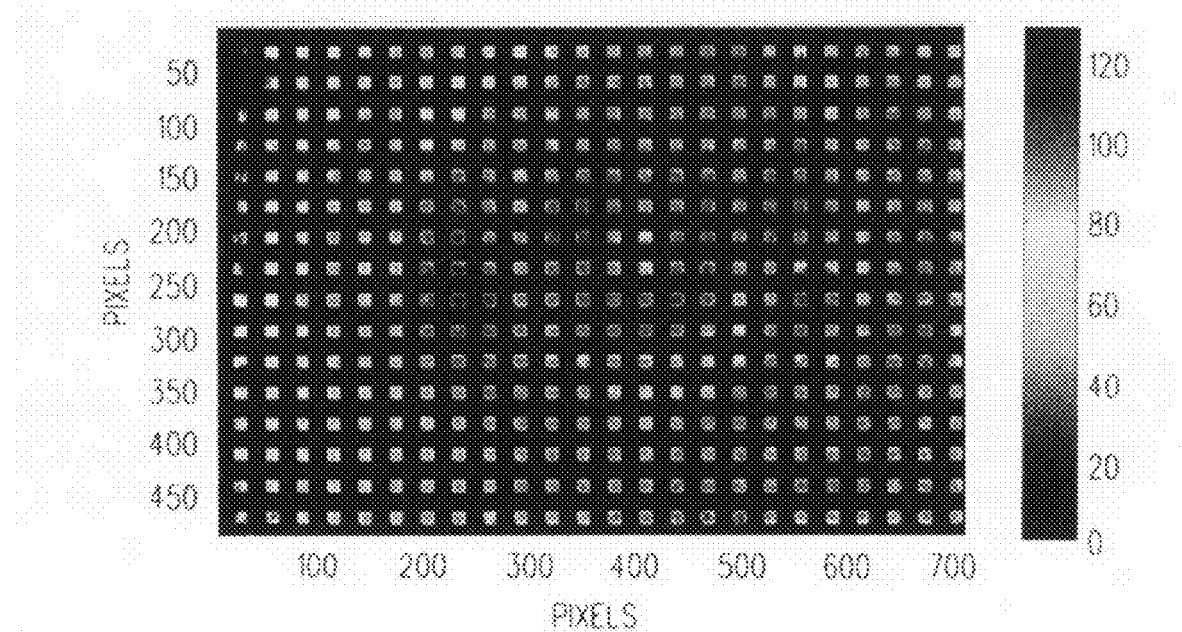
Figure 14B:
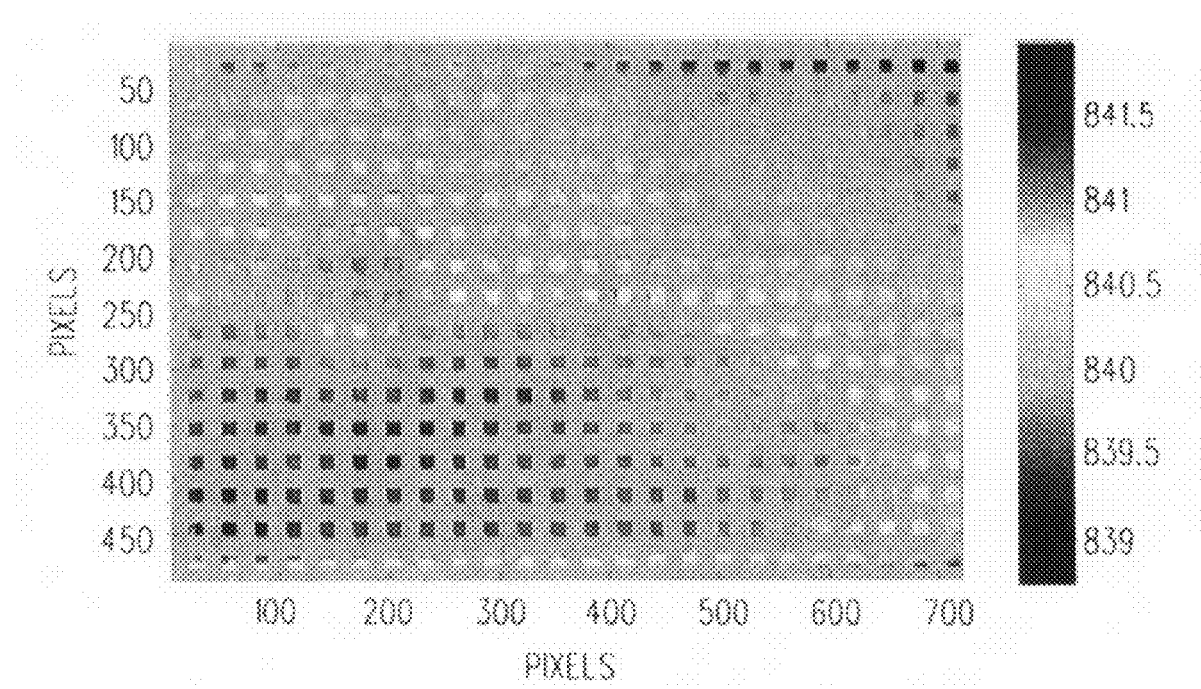

In this experiment, the data processing device 116 processed the spectral image stack by summing-up the images near the resonant wavelengths. Similar, to what had been demonstrated in the single well optical interrogation system 100, the spectral images where processed on a pixel-by-pixel basis. The resulting wavelength image and amplitude image which did not have parasitic interference fringes are respectively shown in FIGS. 14A and 14B. The wavelength image indicates that the wells located in the first and last rows of the microplate 104 exhibited a high intra-well wavelength gradient. While, the amplitude image clearly identified the defective wells in the first column of the microplate 104 (note: these defects were caused by the master used to make microplate 104). As can be seen, the 2D images can be useful for identifying defects and generating accurate positions to enable ROI based detection. This capability is particularly important for pin printed in-well referencing applications.

Figure 15:
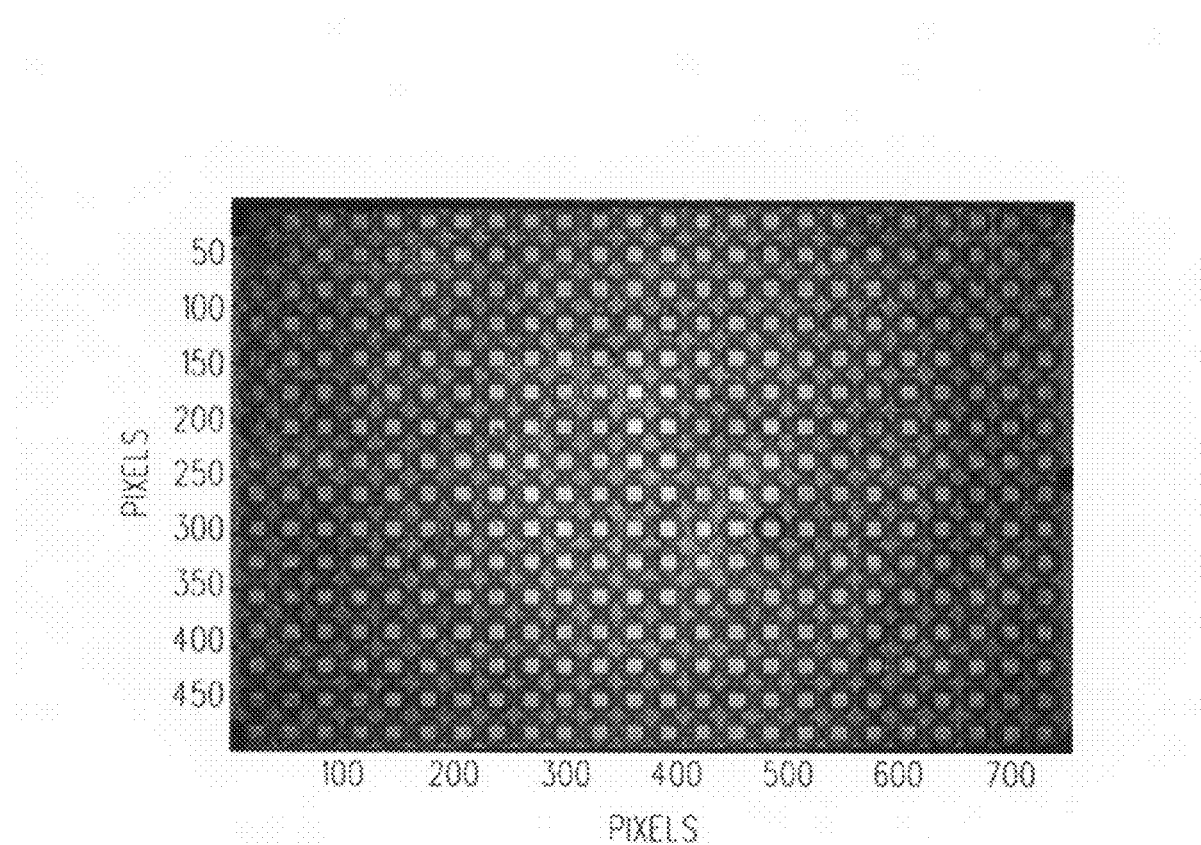

If desired, the optical interrogation system 100 can be quickly converted into a machine vision system by configuring the illumination system to be a fiber coupled broadband source and then integrating the spectral images so one can for example perform position alignments or on-line inspections of microplates 104 (see FIG. 15). In addition, another important optical imaging modality that can be performed by the optical interrogation system 100 is fluorescence imaging. To enable this, the optical interrogation system 100 would need to have laser excitation optics, fluorescent filters and dichroic mirrors added in order to detect fluorescence signals. As can be seen, there are many variations of the swept wavelength imaging optical interrogation system 100 which can be derived within the scope of the present invention. For instance, with the availability of widely tunable light sources and filters, this spectral imaging technique can be used to interrogate the small area sensor chips commonly used in the imaging SPR technique.

Discussion/Alternatives

The optical interrogation system 100 as discussed above is independent of plate format. Thus, the benefits of such a universal reader approach in terms of manufacturing costs and services should be readily apparent. Plus, due to the different nature of high throughput scanning (HTS) assays and kinetics assays, the ROI based optical interrogation system 100 could be easily tailored to address these specific needs. In constrast, the pixel-based optical interrogation system 100 enables label-free microarray based assays like label-free imaging of protein and peptide microarrays. Plus, the pixel-based optical interrogation system 100 provides spatially resolved information which is important since a label-free image can be used to automatically detect grating locations, reference areas, immobilization areas and defects on the interrogated biosensor(s) 102. In addition, the pixel-based optical interrogation system 100 also brings new capabilities to cell assay applications including assays in high throughput, kinetics, and high resolution imaging formats.

Furthermore, the pixel-based optical interrogation system 100 can be used to enable high content screening (HCS) which is a growing market.

To help reduce the bottle neck in data processing, the optical interrogation system 100 can if desired incorporate frame grabbers which have powerful embedded FPGAs to function as an interface between the camera 126 and the data processing device 116. FPGA is highly efficient in handling parallel operations. A second possible option is to closely integrate FPGA and processing electronics into the CMOS camera 126, making it a "smart camera". Besides this embedded processing, emerging computer technology such as FPGA accelerated coprocessor potentially offers yet another alternative. Moreover, the arrival of 64 bit operating system provides an additional boost for software development.

The modular nature of the optical interrogation system 100 makes it relatively straightforward to assemble and perform assays. Unlike SPRI and imaging ellipsometry systems, which must operate at a large oblique incident angle, the interrogation angle of the optical interrogation system 100 is flexible and it can be close to normal incidence. Therefore, the optical interrogation system 100 can be made more compact, stable, and easy to use (e.g., see the compact optical interrogation system 100 shown in FIG. 2).

Those skilled in the art will readily appreciate that the spatial resolution of the optical interrogation system 100 along the grating vector is going to be limited by the leakage coefficient of the WGC biosensor 102. In other words, the leakage coefficient determines the propagation distance of the guided wave before it is coupled back to free space. To address this problem, a deep grating structure (>50 nm) within the WGC biosensor 102 can be used if desired to increase the leakage coefficient and hence the spatial resolution. In practice, the spatial resolution on the order of 100 μm could be achieved. In addition, one can further improve the spatial resolution of the optical interrogation system 100 by using a TE mode of interrogation.

Moreover, those skilled in the art will readily appreciate that the optical interrogation system 100 is built upon a swept wavelength optical interrogation technology where a 2-D label free image is extracted from a series of high speed spectral images of the biosensor(s) 102 without mechanical scanning. The image acquisition speed needed to obtain the "data cube" can be faster than 1 second and can be achieved by using a commercially available high speed CMOS imager 126. While, the real-time processing of the spectral "data cube" is feasible with FPGA 116 and micro-processors 116. Plus, the imaging area of the optical interrogation system 100 can be varied by choosing the magnification of the imaging lens. And, the field of view of the optical interrogation system 100 can be as large as an entire standard 96, 384, or 1536-well microplate without any physical adjustment. Furthermore, a high spatial resolution can be achieved by using a microscope or telecentric lens. Some additional features/capabilities of the optical interrogation system follows:

1. The optical interrogation system 100 is compatible with the practically important WGC based biosensors.

2. The optical interrogation system 100 has fast image acquisition and data processing, preferably within 1 second.

3. The optical interrogation system 100 may utilize a tunable laser 106 which is a mode-hop free, swept wavelength tunable laser 106. For example, the tunable laser 106 can have a wavelength tuning range between 2 nm and 15 nm and a tuning speed between 0.1 nm and 1000 nm/sec.

4. The optical interrogation system 100 may utilize a wavelength tracking device 112 which includes a Mach-Zehnder interferometer 140 which has a free spectral range of 1 to 100 pm, and a wavelength referencing device such as an athermalized etalon 142.

5. The optical interrogation system 100 may utilize illumination optics 122 which include a collimating lens, curved reflective mirror, or stacked modules of collimators.

6. The optical interrogation system 100 may utilize an imaging system 124 which includes a telecentric lens and a focal plane array detector, such as a CMOS or CCD 2-D imaging device 126. For instance, the 2-D imaging devices 126 can have frame rates of 100 fps, 500 fps, 1000 fps, 2000 fps etc. . . .

7. The optical interrogation system 100 may interrogate one or more WGC biosensors 102. The WGC biosensors 102 (which typically has a grating depth deeper than 10 nm, 50 nm. . . . ) can be fabricated within the bottom of standard microplates or within substrates of any sizes.

8. The optical interrogation system 100 can have an imaging area corresponding to all of the biosensors 102 within the microplate 104. Or, the optical interrogation system 100 can have an imaging area corresponding to a single WGC biosensor 102 (which has an area of the size of, for example $10 \times 10$ mm$^2$, or $1 \times 1$ mm$^2$) within the microplate 104.

Although several embodiments of the present invention have been illustrated in the accompanying Drawings and described in the foregoing Detailed Description, it should be understood that the invention is not limited to the embodiments disclosed, but is capable of numerous rearrangements, modifications and substitutions without departing from the spirit of the invention as set forth and defined by the following claims.

The invention claimed is:

1. An interrogation system comprising:
   a tunable laser that has a tuning range wherein an optical beam is emitted therefrom which has a predetermined sequence of distinct wavelengths over a predetermined time period;
   illumination optics that converts the optical beam into one or more interrogation beams which illuminate one or more biosensors;
   imaging optics that collects an image from the illuminated one or more biosensors;
   a 2-D imaging device that obtains a sequence of the collected images each of which corresponds with one of the distinct wavelengths of the optical beam emitted from said tunable laser; and
   a data processing device that receives the collected images and processes the collected images to:
      determine whether or not there was a biochemical interaction on each of the one or more biosensors;
      locate sensor region(s) and/or reference region(s) on each of the one or more biosensors;
      remove defect regions on each of the one or more biosensors; and/or
      calibrate a uniformity of surface chemistry and target molecule immobilizations on each of the one or more biosensors.

2. The interrogation system of claim 1, further comprising a wavelength tracking device which tracks the distinct wavelengths of the optical beam emitted from said tunable laser.

3. The interrogation system of claim 2, wherein said wavelength tracking device includes a fiber Mach-Zehnder interferometer and an athermalized etalon.

4. The interrogation system of claim 2, wherein said wavelength tracking device includes a grating coupled waveguide with a chirped period, where the grating coupled waveguide is illuminated by one of the interrogation beams and the corresponding image is obtained by said 2-D imaging device and processed by said data processing device.

5. The interrogation system of claim 1, further comprising a power tracking device which tracks the power of said tunable laser.

6. The interrogation system of claim 1, wherein said tunable laser is a mode-hop free swept wavelength tunable laser.

7. The interrogation system of claim 1, wherein said illumination optics are setup such that each of the one or more interrogation beams has a substantially flat wavefront.

8. The interrogation system of claim 1, wherein said illumination optics are setup such that of each of the one or more interrogation beams has a wavefront that conforms to a surface of a microplate which contains the one or more biosensors.

9. The interrogation system of claim 1, where said imaging optics include a telecentric lens.

10. The interrogation system of claim 1, wherein said 2-D imaging device further includes;
   a charge coupled device (CCD)) camera with a global shutter; or
   a complementary metal oxide semiconductor (CMOS) camera with a global shutter.

11. The interrogation system of claim 1, wherein each of the one or more biosensors is a waveguide grating coupler biosensors.

12. A method for interrogating one or more biosensors said method comprising the steps of:
   emitting an optical beam which has a predetermined sequence of distinct wavelengths over a predetermined time period;
   converting the optical beam into one or more interrogation beams which illuminates one or more biosensors;
   collecting an image from the illuminated one or more biosensors;
   obtaining a sequence of the collected images each of which corresponds with one of the distinct wavelengths of the emitted optical beam; and
   processing the collected images, wherein a data processing device is used to process the collected images to:
      determine whether or not there was a biochemical interaction on each of the one or more biosensors;
      locate sensor region(s) and/or reference region(s) on each of the one or more biosensors;
      remove defect regions on each of the one or more biosensors; and/or
      calibrate a uniformity of surface chemistry and target molecule immobilizations on each of the one or more biosensors.

13. A method for interrogating one or more biosensors, said method comprising the steps of:
   emitting an optical beam which has a predetermined sequence of distinct wavelengths over a predetermined time period;
   converting the optical beam into one or more interrogation beams which illuminate one or more biosensors;
   collecting an image from the illuminated one or more biosensors;
   obtaining a sequence of the collected images each of which corresponds with one of the distinct wavelength of the emitted optical beam; and
   processing the collected images to locate sensor region(s) and/or reference region(s) on each of the one or more biosensors.

14. The method of claim 13, further comprising, a step of tracking the distinct wavelengths of the emitted optical beam.

15. The method of claim 13, further comprising a step of tracking the power of a tunable laser which emits optical beam.

16. The method of claim 13, wherein an mode-hop free swept wavelength tunable laser is used to emit the optical beam.

17. The method of claim 13, wherein said converting step includes a step of forming each of the one or more interrogation beams so they have a substantially flat wavefront.

18. The method of claim 13, wherein said convening, step further includes a step of forming each of the one or more interrogation beams so they conform to a surface of a microplate which contains the one or more biosensors.

19. The method of claim 13, wherein a telecentric lens is used to collect the image from the illuminated one or more biosensors.

20. The method of claim 13, wherein a 2-D imaging device is used to obtain a sequence of the collected n ages each of which corresponds with one of the distinct wavelengths of the emitted optical beam.

21. The method of claim 13, wherein each of the one or more biosensors is a waveguide grating coupler biosensor.

22. A method for interrogating one or mere biosensors said method comprising the steps of;
   emitting an optical beam which has a predetermined sequence of distinct wavelength over a predetermined time period;
   converting the optical beam into one or more interrogation beams which illuminate one or more biosensors;
   collecting an image from the illuminated one or more biosensors;
   obtaining a sequence of the collected images each of which corresponds with one of the distinct wavelengths of the emitted optical beam; and
   processing the collected images to remove defect regions on each of the one or more biosensors.

23. A method for interrogating one or more biosensors, said method comprising the steps of:
   emitting an optical bean which has a predetermined sequence of distinct wavelengths over a predetermined time period;
   converting the optical be in into one or more interrogation beams which illuminate one or more biosensors;
   collecting an image from the illuminated one or more biosensors;
   obtaining a sequence of the collected images each of which corresponds with one of the distinct wavelengths of the emitted optical beam; and
   processing the collected images to calibrate a uniformity of surface chemistry and target molecule immobilizations on each of the one or more biosensors.

* * * * *

UNITED STATES PATENT AND TRADEMARK OFFICE
CERTIFICATE OF CORRECTION

PATENT NO. : 7,599,055 B2  Page 1 of 1
APPLICATION NO. : 11/711207
DATED : October 6, 2009
INVENTOR(S) : Jacques Gollier et al.

It is certified that error appears in the above-identified patent and that said Letters Patent is hereby corrected as shown below:

| Col. | Line | Description |
|---|---|---|
| 15 | 34 | Reads: "beams which illuminates one or more..." should read "beams which illuminate one or more..." |
| 16 | 2 | Reads: "corresponds with one of the distinct wavelength..." should read "corresponds with one of the distinct wavelengths..." |
| 16 | 12 | Reads: "...wherein an mode-hop free" should read "...wherein a mode-hop free" |
| 16 | 18 | Reads: "...wherein said convening, step" should read "...wherein said converting, step" |
| 16 | 26 | Reads: "...collected n ages each of" should read "...collected images each of" |
| 16 | 31 | Reads: "...or mere biosensors said" should read "...or more biosensors said" |
| 16 | 34 | Reads: "sequence of distinct wavelength over..." should read "sequence of distinct wavelengths over..." |
| 16 | 47 | Reads: "emitting an optical bean which..." should read "emitting an optical beam which..." |
| 16 | 50 | Reads: "converting the optical be in into..." should read "converting the optical beam into..." |

Signed and Sealed this

First Day of December, 2009

David J. Kappos
*Director of the United States Patent and Trademark Office*